United States Patent [19]

Dahmen et al.

[11] Patent Number: 5,409,771

[45] Date of Patent: Apr. 25, 1995

[54] AQUEOUS-LIQUID AND BLOOD-ABSORBING POWDERY RETICULATED POLYMERS, PROCESS FOR PRODUCING THE SAME AND THEIR USE AS ABSORBENTS IN SANITARY ARTICLES

[75] Inventors: Kurt Dahmen, Mönchengladbach-Rheydt; Richard Mertens, Krefeld, both of Germany

[73] Assignee: Chemische Fabrik Stockhausen GmbH, Krefeld, Germany

[21] Appl. No.: 966,047

[22] PCT Filed: Nov. 20, 1990

[86] PCT No.: PCT/EP90/01981

§ 371 Date: Dec. 29, 1992

§ 102(e) Date: Dec. 29, 1992

[87] PCT Pub. No.: WO92/00108

PCT Pub. Date: Jan. 9, 1992

[30] Foreign Application Priority Data

Jun. 29, 1990 [DE] Germany .................. 40 20 780.3

[51] Int. Cl.[6] .............................................. B32B 5/16
[52] U.S. Cl. ............................... 428/327; 428/407; 524/52; 524/108; 524/280; 524/729; 525/329.7; 525/330.1; 525/383
[58] Field of Search ............... 524/52, 280, 729, 108; 525/329.7, 330.1, 383; 428/327, 407

[56] References Cited

U.S. PATENT DOCUMENTS

| | | | |
|---|---|---|---|
| 2,851,434 | 9/1958 | Jones et al. | 524/280 X |
| 4,183,884 | 1/1980 | Wichterle et al. | 524/280 X |
| 4,813,945 | 3/1989 | Le-Khac | 604/367 |
| 4,824,901 | 4/1989 | Alexander et al. | 524/556 X |
| 4,985,518 | 1/1991 | Alexander et al. | 524/556 X |
| 5,151,465 | 9/1992 | Le-Khac | 524/556 X |
| 5,171,781 | 12/1992 | Farrar et al. | 524/556 X |

FOREIGN PATENT DOCUMENTS 239223 2/1987 European Pat. Off. .
361842 9/1989 European Pat. Off. .

*Primary Examiner*—Judy M. Reddick
*Attorney, Agent, or Firm*—Sprung Horn Kramer & Woods

[57] ABSTRACT

The present invention relates to a powdery, water-insoluble, cross-linked resin which absorbs aqueous or serous liquids as well as blood and is composed of a) 55 to 99.9%-wt. polymerized, unsaturated, polymerizable, acid-groups-containing monomers which are neutralized to the extent of at least 25 mol-%, b) 0 to 40%-wt. polymerized, unsaturated monomers copolymerizable with a), c) 0.1 to 5.0%-wt. of a cross-linking agent, and d) 0 to 30%-wt. of a water-soluble polymer, whereby the weight amounts a) to d) relate to anhydrous polymer. The polymer is characterized by the fact that the resin powder has been coated with 0.1 to 5%-wt. of an alkylene carbonate, relative to resin powder, and heated to a temperature of 150° to 300° C. The present invention further relates to a method of producing said polymer and to the use thereof in sanitary articles, such as diapers and the like, and in absorbent constructions consisting of hydrophilic fibers and absorbing resin.

15 Claims, No Drawings

AQUEOUS-LIQUID AND BLOOD-ABSORBING POWDERY RETICULATED POLYMERS, PROCESS FOR PRODUCING THE SAME AND THEIR USE AS ABSORBENTS IN SANITARY ARTICLES

The present invention relates to powdery, cross-linked polymers absorbing aqueous liquids and blood (superabsorbers) and having improved properties with regard to swelling and retention capacity for aqueous liquids under load; to a process for the manufacture of said polymers as well as to the use thereof in absorbent sanitary articles, such as diapers, in the adult incontinence, feminine hygiene, and for wound dressing.

Superabsorbers are water-insoluble, cross-linked polymers which, under swelling and formation of hydrogels, are capable of absorbing large amounts of aqueous liquids and body liquids, such as urine or blood, and of retaining the absorbed amount of liquid under a certain pressure/load. Owing to said characteristic absorption properties the polymers are mainly used for incorporating them in sanitary articles, for example, diapers and sanitary napkins.

The superabsorbers which are commercially available today are cross-linked polyacrylic acids or cross-linked starch-acrylic-acid-graft-polymers the carboxyl groups of which are partially neutralized with sodium hydroxide solution or caustic potash.

In principle, the powdery superabsorbers are manufactured by two methods:

According to the first method, partially neutralized acrylic acid in aqueous solution in the presence of a multi-functional cross-linking agent is converted into a gel by radical polymerization, which is then comminuted, dried, ground, and screened out to the desired particle size. This solvent polymerization may either be carried out continuously or discontinuously. The patent literature discloses a wide spectrum of variations with respect to concentration ratios, temperature, kind and amount of cross-linking agents and initiators. Typical methods are described, for example, in U.S. Pat. Nos. 4,286,082 and 4,076,663 and German patent No. 27 06 135.

The second method is the inverse suspension or emulsion polymerization. In this process, an aqueous, partially neutralized acrylic acid solution is dispersed in a hydrophobic organic solvent by means of protective colloids or emulsifiers, and the polymerization is started by radical initiators. After completion of the polymerization, the water is azeotropically removed from the reaction mixture and the polymeric product filtered off and dried. The cross-linking reaction may be effected by incorporating a polyfunctional cross-linking agent, which is dissolved in the monomer solution, by polymerization, and/or by reacting suitable cross-linking agents with functional groups of the polymer during one of the production steps. The process is described, for example, in U.S. Pat. No. 4,340,706 and German patent Nos. 37 13 601 and 28 40 010.

Initially, only the high swelling capacity on contact with liquids, also referred to as free swelling capacity, had been the main factor in the development of superabsorbers; later it was found, however, that it is not only the amount of absorbed liquid that is important but also the stability of the swollen gel.

However, the absorbency, also referred to as swellability or free swelling capacity, on the one hand, and the gel strength of a cross-linked polymer, on the other hand, represent contrary properties: this has been known from U.S. Pat. No. 3,247,171 and U.S. Pat. No. Re. 32,649. This means that polymers with a particularly high absorbency exhibit a poor strength of the swollen gel so that the gel is deformable under pressure (e.g., the load of a body) and prevents further liquid distribution and absorption. According to U.S. Pat. No. Re 32,649 a balanced relation between absorptivity (gel volume) and gel strength should be aimed at so as to ensure liquid absorption, liquid transport, and dryness of the diaper and the skin when using such superabsorbers in a diaper construction. In this connection, not only the polymer's capacity of retaining a liquid under subsequent pressure, after swelling freely first, is of importance but also the fact that liquids are absorbed even against a simultaneously acting pressure, i.e., during the liquid absorption; this is the case in practice when a baby or person sits or lies on a sanitary article or when shear forces are acting, e.g., by movements of legs. In the European patent No. 0 339 461, this special absorption property is referred to as absorption under load.

The only way to meet the increasing trend of reducing the size and thickness of sanitary articles for esthetic and environmental reasons (reduction of waste in the land fill) is to reduce the large-volume fluff pulp in diapers and to increase the portion of super-absorber at the same time. For this reason, the super-absorber has to take over additional functions with respect to liquid absorption and transport thereof, which previously were performed by the fluff pulp and which cannot be accomplished satisfactorily by the known superabsorbers.

It is accordingly the object of the present invention to provide superabsorbing polymers exhibiting to a particularly high degree the characteristic property combination, such as high retention capacity, high gel strength and high absorbency under load. It is yet another object of the present invention to provide a process of producing said absorbents.

This object is achieved by the characterizing features of claim 1. It has been found surprisingly that the absorption under load can considerably be improved by coating a particle-shaped absorber resin with 0.1 to 5%-wt. alkylene carbonates and subsequent heating to 150° to 300° C., and that high retention values and high gel strengths are achieved at the same time.

The surface treatment of water-absorbing resins is known. For example, U.S. Pat. No. 4,043,952 proposes to use polyvalent metal compounds to improve the dispersibility in water, and U.S. Pat. No. 4,051,086 proposes the use of glyoxal to improve the absorption rate. The secondary treatment of resins with crosslinking agents comprising bi- or polyfunctional groups capable of reacting with the carboxyl or carboxylate groups or other groups contained in the polymer is described in EP No. 0 083 022 (to improve the dispersibility in water and the absorbency), DE-OS No. 33 31 644 (to improve the resistance to salt solutions at a high water absorption rate), DE-OS 35 07 775 (to increase the salt resistance with good liquid absorption and gel rigidity), DE-OS 35 23 617 (to improve the flowability and prevent agglomeration), DE-OS 36 28 482 (to improve the water absorption when repeatedly used), and EP 0 349 240 (to achieve a balance between absorbency and absorption rate as well as gel strength and suction force).

In these cases, the powder is either mixed with the components directly, optionally with using small amounts of water and solvent, or dispersed in an inert solvent, or polymers comprising 10 to 40%-wt. of water are dispersed in a hydrophilic or hydrophobic solvent and mixed with the cross-linking agent afterwards or simultaneously. Suitable cross-linking agents include polyglycidyl ethers, halo epoxy compounds, polyols, polyamines, or polyisocyanates. Additionally polyfunctional aziridine compounds, alkyl-di-(tri)-halogenides, and oil-soluble polyepoxy compounds are mentioned in DE-OS 33 14 019, EP 0 317 106 (both to achieve a high absorption amount and high absorption rate), and DE-OS 37 37 196 (high absorbency and high absorption rate with simultaneous high gel strength). According to DE-OS 35 03 458 (to obtain a polymer with a good water absorption capacity, high water absorption rate and high gel strength of a non-tacky gel) the application of a cross-linking agent on a polymeric resin is effected in the presence of an inert inorganic powdery material, such as $SiO_2$, without using organic solvents. All these processes have in common that a temperature treatment of the resins is carried out subsequently, and that the cross-linking agents used for the surface treatment have at least two functional groups.

The above-mentioned prior art gives no indication to the fact that a surface treatment of absorbing resins can increase the absorbency under load, or that the property combination of high retention capacity, high gel strength and high absorbency under load can be achieved simultaneously.

Most of the cross-linking agents used to date exhibit disadvantageous toxic properties. Therefore, they cannot be used in the sensitive field of hygiene because they are injurious to health. In addition to the relatively harmless risk of a skin irritation, epoxy, glycidyl and organic halogen compounds as well as isocyanates have a sensitising effect and frequently a cancerogenic and mutagenic potential. Polyamines cannot be used because of possible nitrosamine formation. In any case, when used in diapers and other sanitary articles, unreacted portions of the toxicologically critical cross-linking agents have to be removed carefully from the polymeric resins. This involves additional and expensive cleaning processes which increase the cost of the known production processes and render them uneconomic.

According to the present invention the following may be used as alkylene carbonates, e.g., 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, or 1,3-dioxepan-2-one. 1,3-dioxolan-2-one and 4-methyl-1,3-dioxolan-2-one are particularly preferred.

The water-absorbing resin which may be used for the coating is obtained by polymerizing 55 to 99.9%-wt. of monomers with acid groups, e.g., acrylic acid, methacrylic acid, 2-acrylamido-2-methylpropane sulfonic acid, or mixtures of said monomers. The acid groups are neutralized to the extent of at least 25 mol-%, e.g., as sodium, potassium or ammonium salts. The neutralization degree preferably is of the order of at least 50 mol-%. A particularly preferred resin is formed of cross-linked acrylic acid or methacrylic acid which is neutralized by 50 to 80 mol -%.

As further monomers for the production of the water-absorbing resins 0 to 40%-wt. acrylamide, methacrylamide, hydroxyethyl acrylate, dimethylaminoalkyl (meth)-acrylate, dimethylaminopropyl acrylamide, or acrylamidopropyl trimethylammonium chloride may be used. Percentages above 40% of these monomers deteriorate the swell capacity of the resins.

As cross-linking agent all compounds may be used which have at least two ethylenically unsaturated double-bonds or one ethylenically unsaturated double-bond and one functional group reactive towards acid groups or several functional groups reactive towards acid groups. Examples thereof include: acrylates and methacrylates of polyols, such as butanediol-diacrylate, hexanediol-dimethacrylate, polyglycol-diacrylate, trimethylolpropane triacrylate, or allyl acrylate, diallyl acrylamide, triallyl amine, diallyl ether, methylenebisacrylamide, or N-methylolacrylamide.

0 to 30%-wt. partially or completely saponified polyvinyl alcohol, polyvinyl pyrrolidone, starch or starch derivatives, polyglycols, or polyacrylic acids may be comprised as water-soluble polymers in the water-absorbing resin. The molecular weight of said polymers is not critical provided that they are water-soluble. Preferred water-soluble polymers are starch or polyvinyl alcohol, or mixtures of said polymers. The preferred content of said water-soluble polymers in the water-absorbing resin is in the range of 1 to 5%-wt., in particular if starch and/or polyvinyl alcohol are present as soluble polymers. The water-soluble polymers may be present as graft polymers with the acid-groups-containing polymers.

In addition to resins obtained by the cross-linking polymerization of partially neutralized acrylic acid those are preferably used which additionally comprise portions of graft-polymerized starch or of polyvinyl alcohol.

There are no specific limitations with respect to the particle shape of the absorbing resin used. The polymer may be spherical obtained by inverse suspension polymerization, or may derive from irregularly shaped particles obtained by drying and pulverizing the gel mass of the solvent polymerization. Usually, the particle size is between 20 and 2000 μm, preferably between 50 and 850 μm.

For the coating, the water-absorbing resins may be mixed with an aqueous-alcoholic solution of the alkylene carbonate. The amount of alcohol is determined by the solubility of the alkylene carbonate and is kept as low as possible for technical reasons, e.g., protection against explosions. Suitable alcohols are methanol, ethanol, butanol, or butyl glycol as well as mixtures of said alcohols. The preferred solvent is water which is used in an amount of 0.3 to 5.0%-wt., relative to resin. It is also possible to apply the alkylene carbonate from a powder mixture, e.g., with an inorganic carrier material, such as $SiO_2$.

To achieve the desired properties the alkylene carbonate has to be distributed evenly on the resin powder. For this purpose, mixing is effected in suitable mixers, e.g., fluidized bed mixers, paddle mixers, milling rolls, or twin-worm-mixers.

It is also possible to carry out the coating of the absorber resin during one of the process steps in the production of the polymeric resin. A particularly suitable process for this purpose is the inverse suspension polymerization.

The thermal treatment which follows the coating is carried out at 150° to 300° C.; if the preferred alkylene carbonates are used at 180 to 250° C. The temperature depends on the dwell time and the kind of alkylene carbonate. At a temperature of 150° C. the thermal treatment must be carried out for several hours, whereas at 250° C. a few minutes, e.g., 0.5 to 5 minutes, are sufficient to achieve the desired properties. The thermal treatment may be carried out in conventional dryers or ovens; examples thereof include rotary kilns, fluidized bed dryers, disk dryers, or infrared dryers.

The polymers according to the present invention may be manufactured on the large scale by continuous or discontinuous processes. The agents according to the present invention may be used for a variety of applications. If they are used, for example, as absorbing material in sanitary napkins and diapers, or for wound dressing purposes, they have the property to absorb rapidly large amounts of menstrual blood, urine or other body liquids. The absorptivity and absorption rate under a simultaneously acting pressure load is by far higher than in the known products. Since the agents according to the present invention retain the absorbed liquids even under load, they are particularly easy to use. They are particularly suitable for the use at concentrations that—relative to hydrophilic fiber material, e.g., fluff pulp—are higher than the ones possible to use to date; they have excellent absorption properties in constructions comprising 98 to 20%-wt. hydrophilic fibers and 2 to 80%-wt. of the absorbing resin.

The polymers coated according to the present invention are used in absorbent articles for various kinds of application, e.g., by mixing with paper or fluff pulp or synthetic fibers, or distributing the agent between substrates made of paper, fluff pulp or non-woven textiles, or by shaping in carrier materials to form a web.

The alkylene carbonates used according to the present invention for the coating of polymeric resins exhibit no critical toxicological properties.

The superabsorbers obtained by coating with the alkylene carbonates according to the present invention and subsequent heating surprisingly exhibit a considerable improvement in the liquid absorption under load with respect to velocity and total capacity, they have a high gel strength and high retention at the same time. In particular, an extremely high initial liquid absorption rate under load is achieved so that 80% of the total capacity is achieved within only 15 minutes. The absorption under load (AUL) is above 25 g/g under a load of 20 g/cm$^2$, preferably above 27 g/g with retention values (TB) of at least 28 g/g, more preferably above 30 g/g when the absorption is measured with 0.9% sodium chloride solution. The sum of retention and absorption under load is greater than 53 g/g, preferably greater than 60 g/g. The gel strength of the products according to the present invention amounts to at least 2,000 N/m$^2$ at a gel volume of 28 g/g.

Test methods:

To characterize the water-absorbing resin the retention (TB), the absorption under load (AUL) and the shear modulus were measured.

The retention is determined according to the tea bag test method and reported as average value of three measurements. Approximately 200 mg resin are enclosed in a tea bag and immersed in 0.9% NaCl-solution for 20 minutes. Then the tea bag is centrifuged in a centrifuge (diameter: 23 cm; rpm: 1,400) for 5 minutes and weighed. One tea bag without water-absorbing resin is used as blank.

$$\text{Retention} = \frac{\text{Weight} - \text{blank reading}}{\text{Initial weight}} \; (g/g)$$

The absorption under load (pressure load: 20 g/cm$^2$) is determined according to the method described in EP 0 339 461, page 7: The initial weight of superabsorber is placed in a cylinder with sieve bottom and the powder is stressed with a punch exerting a pressure of 20 g/cm$^2$. The cylinder is subsequently placed on a Demand-Absorbency-Tester (DAT) and the superabsorber is allowed to suck 0.9% NaCl-solution for one hour.

The shear modulus is measured by means of a Carri-Med-Stress-Rheometer with a plate-plate-configuration. In order to determine the shear modulus, 1 g water absorbing resin is allowed to swell in 28 g 0.9% NaCl-solution for one hour, then the shear modulus is measured with the swollen gel in dependence on the frequency (0.1–10 Hz). The value at 10 Hz is indicated as storage modulus G'.

The water-absorbing resin powders used in the following examples for coating with an alkylene carbonate were manufactured according to the known processes of the solution or suspension polymerization. All %-indications relate to powder.

EXAMPLE 1

A powdery polyacrylic acid cross-linked with trimethylolpropane triacrylate and present as sodium salt neutralized to the extent of 70 mol-% was screened to 50 to 850 μm (powder A), 100 g of powder A was mixed under strong stirring with a solution of 2.5 g 1,3-dioxolan-2-one, 2.5 g water, and 2.5 g ethanol and subsequently heated in an oven having a temperature of 180° C. for 1 hour.

For comparison purposes 100 g of powder A was mixed with a mixture of 2.5 g water and 2.5 g ethanol and also heated at 180° for 1 hour.

After cooling, the powders were screened to 50 to 850 μm once again; the retention (TB), absorption under load (AUL) and the storage modulus G' were determined:

| | TB g/g | AUL g/g | Sum TB + AUL | G' N/m$^2$ |
|---|---|---|---|---|
| Powder A | 45 | 6 | 51 | 1,200 |
| Example 1 | 41 | 33 | 74 | 2,600 |
| Comparative Example without 1,3-dioxolan-2-one | 45 | 6 | 51 | 1,200 |

EXAMPLE 2 to 4

Three powdery polyacrylic acids cross-linked to different extents, neutralized to the extent of 70 mol-% as sodium salt, (powders B, C, D) were mixed with 1,3-dioxolan- 2-one according to Example 1 and heated in an oven at 180©C for 1 hour:

| | 1,3-dioxolan-2-one % | H$_2$O / % | Ethanol % | TB g/g | AUL g/g |
|---|---|---|---|---|---|
| Powder B | — | | | 39 | 11 |
| Example 2 | 1.5 | 2.0 | 2.0 | 36 | 30 |
| Powder C | — | | | 36 | 13 |
| Example 3 | 1.0 | 2.0 | 2.0 | 34 | 31 |
| Powder D | — | | | 31 | 17 |
| Example 4 | 0.2 | 1.0 | 2.0 | 30 | 30 |
| | | | Sum | | G' |

-continued

| Continuation: | TB + AUL | G' N/m² |
|---|---|---|
| Powder B | 50 | 1,800 |
| Example 2 | 66 | 3,000 |
| Powder C | 49 | 2,300 |
| Example 3 | 65 | 3,200 |
| Powder D | 48 | 4,000 |
| Example 4 | 60 | 4,200 |

EXAMPLE 5 to 8

100 g powder B was mixed with different carbonates, dissolved in a mixture of water and ethanol, and heated in an oven at 215° C.:

| | Carbonate | Quantity Carbonate | Time min. | TB g/g | AUL g/g |
|---|---|---|---|---|---|
| Powder B | — | — | — | 39 | 11 |
| Example 5 | 4-methyl-1,3-dioxolan-2-one | 2 g | 20 | 37 | 31 |
| Example 6 | 1,3-dioxan-2-one | 2 g | 15 | 37 | 30 |
| Example 7 | 4-methyl-1,3-dioxan-2-one | 2 g | 30 | 36 | 33 |
| Example 8 | 4-ethyl-1,3-dioxolan-2-one | 2 g | 20 | 37 | 30 |

| Continuation: | Sum TB + AUL | G' N/m² |
|---|---|---|
| Powder B | 50 | 1,800 |
| Example 5 | 68 | 2,500 |
| Example 6 | 67 | 2,600 |
| Example 7 | 69 | 2,600 |
| Example 8 | 67 | 2,400 |

EXAMPLE 9 to 13

Different amounts of 1,3-dioxolan-2-one or water were mixed with 100 g of powder A and heated in an oven at 180° C. for 1 hour.

| | 1,3-dioxolan-2-one / % | H₂O % | TB g/g | AUL g/g | Sum TB + AUL | G' N/m² |
|---|---|---|---|---|---|---|
| Powder A | — | — | 45 | 6 | 51 | 1,200 |
| Example 9 | 0.5 | 0.5 | 43 | 28 | 71 | 2,350 |
| Example 10 | 1.0 | 1.0 | 41 | 32 | 73 | 2,450 |
| Example 11 | 1.5 | 1.5 | 40 | 34 | 74 | 2,500 |
| Example 12 | 2.0 | 2.0 | 37 | 34 | 71 | 2,700 |
| Example 13 | 3.5 | 3.5 | 32 | 32 | 67 | 2,800 |

EXAMPLE 14 to 19

100 g powder B was mixed with an aqueous 1,3-dioxolan-2-one solution and heated to different temperatures by means of the warm air of a hot-air ventilator. The temperature of the air stream was measured prior to contact with the powder.

| | EC* % | H₂O % | T °C. | Time min | TB g/g | AUL g/g | Sum TB + AUL |
|---|---|---|---|---|---|---|---|
| Powder B | — | — | — | — | 39 | 11 | 50 |
| Example 14 | 2.5 | 2.0 | 215 | 5 | 38 | 28 | 66 |
| Example 15 | 2.5 | 2.0 | 215 | 10 | 36 | 29 | 65 |
| Example 16 | 2.5 | 2.5 | 215 | 20 | 34 | 28 | 62 |
| Example 17 | 1.0 | 1.5 | 250 | 2 | 38 | 29 | 67 |
| Example 18 | 1.0 | 1.0 | 250 | 5 | 36 | 29 | 65 |
| Example 19 | 1.0 | 1.0 | 250 | 10 | 34 | 30 | 64 |

*EC = 1,3-dioxolan-2-one

EXAMPLE 20 to 23

Powdery, cross-linked polyacrylic acids either comprising starch or polyvinyl alcohol, present as sodium salt in neutralized form to the extent of 70 tool-%, (powders E, F, G, H) were mixed with aqueous-alcoholic solutions of 1,3-dioxolan-2-one and heated in an oven at 170° C. for two hours.

| | PVA¹ | starch | EC | H₂O | EtOH² | TB g/g | AUL g/g |
|---|---|---|---|---|---|---|---|
| | % | | | % | | | |
| Powder E | 3.5 | — | — | | | 45 | 7 |
| Example 20 | 3.5 | — | 2 | 1 | 0 | 37 | 30 |
| Powder F | 4.5 | — | — | | | 45 | 6 |
| Example 21 | 4.5 | — | 1 | 1 | 1 | 41 | 28 |
| Powder G | — | 3.5 | — | | | 41 | 7 |
| Example 22 | — | 3.5 | 1.5 | 1 | 1 | 35 | 29 |
| Powder H | — | 6.0 | — | | | 40 | 7 |
| Example 23 | — | 6.0 | 1 | 1 | 1 | 34 | 29 |

| Continuation: | Sum TB + AUL | G' N/m² |
|---|---|---|
| Powder E | 52 | 1,300 |
| Example 20 | 67 | 2,400 |
| Powder F | 51 | 1,200 |
| Example 21 | 69 | 2,100 |
| Powder G | 48 | 1,600 |
| Example 22 | 64 | 2,200 |
| Powder H | 47 | 1,600 |
| Example 23 | 63 | 2,300 |

¹PVA = polyvinyl alcohol
²EtOH = Ethanol

EXAMPLE 24 to 26

Cross-linked, powdery copolymers of acrylic acid/2-acrylamido-2-methylpropane sulfonic acid (powder K), acrylic acid/acrylamide (powder L), and acrylic acid/dimethylaminopropyl acrylamide (powder M) were mixed with aqueous-ethanolic solutions of 1,3-dioxolan-2-one and heated in an oven at 215° C. for 15 minutes.

| | AA / comonomer⁽¹⁾ %-wt. | EC | H₂O % | EtOH⁽¹⁾ | TB g/g |
|---|---|---|---|---|---|
| Powder K | 65 / 35 AMPS | — | | | 35 |
| Example 24 | " | 0.3 | 1.0 | 2.0 | 34 |
| Powder L | 80 / 20 AcA | — | | | 37 |
| Example 25 | " | 0.5 | 1.0 | 1.0 | 34 |
| Powder M | 90 / 10 DIMAPA | — | | | 39 |
| Example 26 | " | 0.5 | 1.0 | 1.0 | 36 |

| Continuation: | AUL g/g | Sum TB + AUL | G' N/m² |
|---|---|---|---|
| Powder K | 7 | 42 | 2,700 |
| Example 24 | 29 | 63 | 3,450 |
| Powder L | 6 | 43 | 1,900 |
| Example 25 | 28 | 62 | 3,000 |
| Powder M | 6 | 45 | 1,600 |
| Example 26 | 28 | 64 | 2,350 |

⁽¹⁾AMPS = 2-acrylamido-2-methylpropane sulfonic acid
AcA = acrylamide
DIMAPA = dimethylaminopropyl acrylamide
EC = 1,3-dioxolan-2-one
EtOH = ethanol

EXAMPLE 27 to 30

The use of the water-absorbing resins according to the present invention was tested in sandwiched constructions of fluff pulp and water-absorbing resin. Round constructions (diameter: 5.8 cm) of three fluff pulp layers and two layers of water-absorbing resin were placed in a Büchner funnel and loaded with 20 g/cm². The Büchner funnel is connected with a reservoir of 0.9% NaCl-solution via a hose. The construction is allowed to suck for 15 minutes or 1 hour, respectively; subsequently it is enclosed in a large tea bag and centrifuged in a drum having a diameter of 23 cm for 5 minutes at 1,400 rpm. The absorption of the resin is calculated as follows:

$$\text{Absorption} = \frac{\text{g (tea bag with fluff/resin)} - \text{g (tea bag with fluff/without resin)}}{\text{Initial weight of resin}}$$

| | Water-absorbing resin from example | Percentage resin in the construction | Absorption g/g 15 min | Absorption g/g 60 min |
|---|---|---|---|---|
| Example 27 | 1 | 40 | 26 | 32 |
| Example 28 | 11 | 40 | 27 | 34 |
| Example 29 | 13 | 40 | 25 | 30 |
| Example 30 | 20 | 40 | 25 | 28 |
| Comparison: | Powder B | 40 | 10 | 16 |
| | Powder D | 40 | 16 | 20 |

We claim:

1. Powdery, water-insoluble, cross-linked polymerized resinous particles capable of absorbing aqueous or serous liquids or water, produced by polymerizing a composition comprising by weight
   (a) 55 to 99.9% of an unsaturated polymerizable monomer containing acid groups, at least 25 mol % of the acid groups being neutralized,
   (b) 0 to 40% of polymerizable unsaturated monomers other than (a),
   (c) 0.1 to 5% of a cross-linking agent, and
   (d) 0 to 30% of a water-soluble polymer, to form water-insoluble resinous particles, coating the particles with 0.1 to 5% their weight on an anhydrous basis of an alkylene carbonate, and heating the coated particles to a temperature of 150° to 300° C.

2. Resinous particles according to claim 1, exhibiting
   (a) a retention of at least 28 g with 0.9%-sodium chloride solution per g of resin,
   (b) an absorption of at least 25 g with 0.9%-sodium chloride solution per g of resin under a load of 20 g/cm$^2$,
   (c) a gel strength, measured as shear modulus, of at least 2,000 N/m$^2$ with a gel volume of 28 g 0.95%-sodium chloride solution per g of resin.

3. Resinous particles according to claim 1, formed of acrylic acid, methacrylic acid, and/or 2-acrylamide-2-methylpropane sulfonic acid as acid-group-containing monomer.

4. Resinous particles according to claim 1, wherein the acid-group-containing monomers are neutralized to at least 50 mol-%.

5. Resinous particles according to claim 1, formed of acrylic acid neutralized to 50 to 80 mol-% as the only acid-group-containing monomer.

6. Resinous particles according to claim 1, wherein the water-soluble polymer is used in concentrations of 1 to 5%-wt.

7. Resinous particles according to claim 1, wherein starch and/or polyvinyl alcohol are used as water-soluble polymers.

8. Resinous particles according to claim 1, wherein 0.2 to 3.5%-wt. of the alkylene carbonate is used.

9. Resinous particles according to claim 8, wherein the alkylene carbonate is selected from the group consisting of 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxepan-2-one.

10. Resinous particles according to claim 8, wherein the alkylene carbonate is selected from the group consisting of 1,3-dioxolan-2-one and 4-methyl-1,3-dioxolan-2-one.

11. Resinous particles according to claim 1, wherein the cross-linking agent contains at least two ethylenically unsaturated double-bonds or one ethylenically unsaturated double bond and at least one functional group reactive towards acid groups.

12. A process for the preparation of powdery, water-insoluble, cross-linked polymerized resinous particles capable of absorbing aqueous or serous liquids or water, which comprises polymerizing a composition comprising by weight
   (a) 55 to 99.9% of monomeric units of an unsaturated polymerizable monomer containing acid groups, at least 25 mol % of the acid groups being neutralized,
   (b) 0 to 40% of polymerizable unsaturated monomers other than (a),
   (c) 0.1 to 5% of a cross-linking agent, and
   (d) 0 to 30% of a water-soluble polymer, to form resinous particles, coating the particles with 0.1 to 5% their weight on an anhydrous basis of an alkylene carbonate, and heating the coated particles to a temperature of 150° to 300° C.

13. A sanitary article for absorbing body liquids including as the absorptive material powdery particles according to claim 1.

14. A sanitary article according to claim 13, wherein such article is a diaper, incontinence article, sanitary napkin or wound dressing.

15. A sanitary article according to claim 13, the article comprising by weight 98 to 20% of hydrophilic fibers and 2 to 80% of the powder resin particles.

* * * * *